United States Patent [19]

Niwa

[11] Patent Number: 5,105,093

[45] Date of Patent: Apr. 14, 1992

[54] APPARATUS FOR MEASURING PARTICLE SIZE DISTRIBUTION BY MAKING USE OF LASER BEAM DIFFRACTION AND SCATTERING

[75] Inventor: Takeshi Niwa, Kyoto, Japan

[73] Assignee: Shimadzu Corporation, Kyoto, Japan

[21] Appl. No.: 628,520

[22] Filed: Dec. 17, 1990

[30] Foreign Application Priority Data

Dec. 18, 1989 [JP] Japan .................................. 1-328736

[51] Int. Cl.$^5$ ........................................... G01N 15/06
[52] U.S. Cl. ................................ 250/574; 250/214 C; 356/336
[58] Field of Search .................... 250/574, 214 C; 356/335, 336, 337, 338, 343

[56] References Cited

U.S. PATENT DOCUMENTS

| | | | |
|---|---|---|---|
| 4,380,392 | 4/1983 | Karabegov et al. | 356/336 |
| 4,781,460 | 11/1988 | Bott | 250/574 |
| 4,796,995 | 1/1989 | Salzman et al. | 356/338 |
| 4,842,406 | 6/1989 | von Bargen | 356/336 |
| 4,893,929 | 1/1990 | Miyamoto | 356/336 |

Primary Examiner—David C. Nelms
Assistant Examiner—S. Allen
Attorney, Agent, or Firm—Armstrong, Nikaido, Marmelstein, Kubovcik & Murray

[57] ABSTRACT

Apparatus for measuring a particle size distribution by analyzing the intensity distribution of light scattered by particles suspended in a medium fluid. The apparatus is provided with not only a photosensor assembly for detecting forward scattered light but also that for detecting sideward and backward scattered light for the purpose of increasing the precision of measurement. Both the photosensor assemblies are temperature-monitored to prevent erroneous measurement due to small temperature-dependent zero-level shifts of photosensors used in the photosensor assemblies. If temperature variations of or a temperature difference between the assemblies exceeds a predetermined value, an alarm signal is generated with the measurement interrupted automatically.

2 Claims, 4 Drawing Sheets

APPARATUS FOR MEASURING PARTICLE SIZE DISTRIBUTION BY MAKING USE OF LASER BEAM DIFFRACTION AND SCATTERING

BACKGROUND OF THE INVENTION

The present invention relates to an optical apparatus for measuring the size distribution of sample particles through an analysis of the intensity distribution of light scattered by the sample particles kept suspended in a medium fluid.

The basic constitution of a conventional exampler of such an apparatus consists, as is illustrated in FIG. 5, essentially of a laser system (not shown) for making a light beam L, a transparent sample vessel 1 made, for instance, as a flow cell through which flows a medium with sample particles dispersed therein, a Fourier transformation lens 2, a photosensor assembly 3 made up of concentrically arrayed semi-circular photosensors 33, and a computer 4. With the sample vessel 1 irradiated by the light beam L, the sample particles dispersed in the flowing medium scatter the light beam L in every direction. In this apparatus, part of the light scattered forward is detected by the photosensors 33, which output data signals reflecting the intensity distribution of the forward scattered light. The computer 4 processes the data signals to derive the size distribution of the sample particles according to an algorithm predetermined on the basis of the theory of the Fraunhofer diffraction or of the Mie scattering.

As to this type of apparatus it is well known that the precision of particle size distribution measurement is increased with increase in the angular region of detectable scattered light. Therefore, more precise measurement capable of obtaining information on the particle size of the order of 0.1 $\mu$m can be achieved by providing the apparatus additionally with photosensors for detecting sideward (scattering angle: 90°) and backward (scattering angle larger than 90°) scattered components of light. However, there are many problems to be solved in detecting also the light scattered at large angles.

The intensity of scattered light decreases with increase in the angle of scattering. The intensity, though it depends also on that of the incident light beam L, usually decreases to such a very low level as 1 lux or lower for large scattering angles reaching 90° or larger. In addition the precision measurement of particle size distribution necessiates the detection of scattered light with an accuracy of 99% or higher. Therefore, small temperature-dependent zero-level drifts of the photosensors used can not be ignored, paraticularly when the measurement is made, as is often the case, for samples which must be kept at a temperature much higher or lower than an ambient temperature. Typical temperature-dependent characteristics of a photodiode commonly used in the photosensors are shown in FIGS. 3 and 4 standing, respectively, for the dark current and for the short-circuit current. In the case of the previously mentioned conventional apparatus, each time a new measurement operation is commenced with a new sample, the apparatus has its zero-level readjusted corresponding to an ambient temperature at that time, but a possible very small zero-level drift due to an ambient temperature variation which may arise during a relatively short period of time of the measurement has been ignored, because the apparatus detects only small-angled forward scattered light having a relatively strong intensity.

OBJECTS AND SUMMARY OF THE INVENTION

The present invention aims at solving the above mentioned problems involved in the precise measurement of particle size distribution, and makes it an object to provide an improved optical apparatus made capable of precisely measuring the size distribution of particles whose smallest size reaches the order of 0.1 $\mu$m.

Another object of the present invention is to make such an improved apparatus prevented from any erroneous measurement caused by temperature variations which may arise during a process of measurement.

To achieve the above objects the apparatus according to the present invention comprises an additional photosensor assembly for the detection of sideward and backward scattered lights, in addition to the conventional constitution in which are included, as is previously mentioned, a light source system, a sample vessel, a Fourier transformation lens, an arciform photosensor assembly for detecting forward scattered light, and a computer. Further, both the additional photosensor assembly (for detecting sideward and backward scattered lights) and the the arciform photosensor assembly (for detecting forward scattered light) are provided with their respective temperature sensors. With the present invention thus constituted, the computer serves both for deriving the size distribution of sample particles from optical data outputted from the two photosensor assemblies and for generating an alarm signal if the temperature of each of the two photosensor assemblies or the temperature difference between them exceeds a predetermined value. With the alarm signal raised, the operation of particle size distribution measurement can manually or automatically be made suspended to readjust the apparatus as to the temperature-dependent zero-level drifts of the photosensors used.

According to the present invention, the two photosensor assemblies, which cover forward, sideward and backward scattered lights, make the apparatus capable of precisely analyzing particle size distribution including very small-sized particles of the order of 0.1 $\mu$m, while the alarm system prevents the apparatus from possible erroneous measurement due to temperature variations which may arise during a process of measurement.

BRIEF DESCRIPTION OF THE DRAWINGS

In the following the present invention is described in further detail on reference to the accompanying drawings in which.

DETAILED DESCRIPTION OF THE IINVENTION

Figure 1:
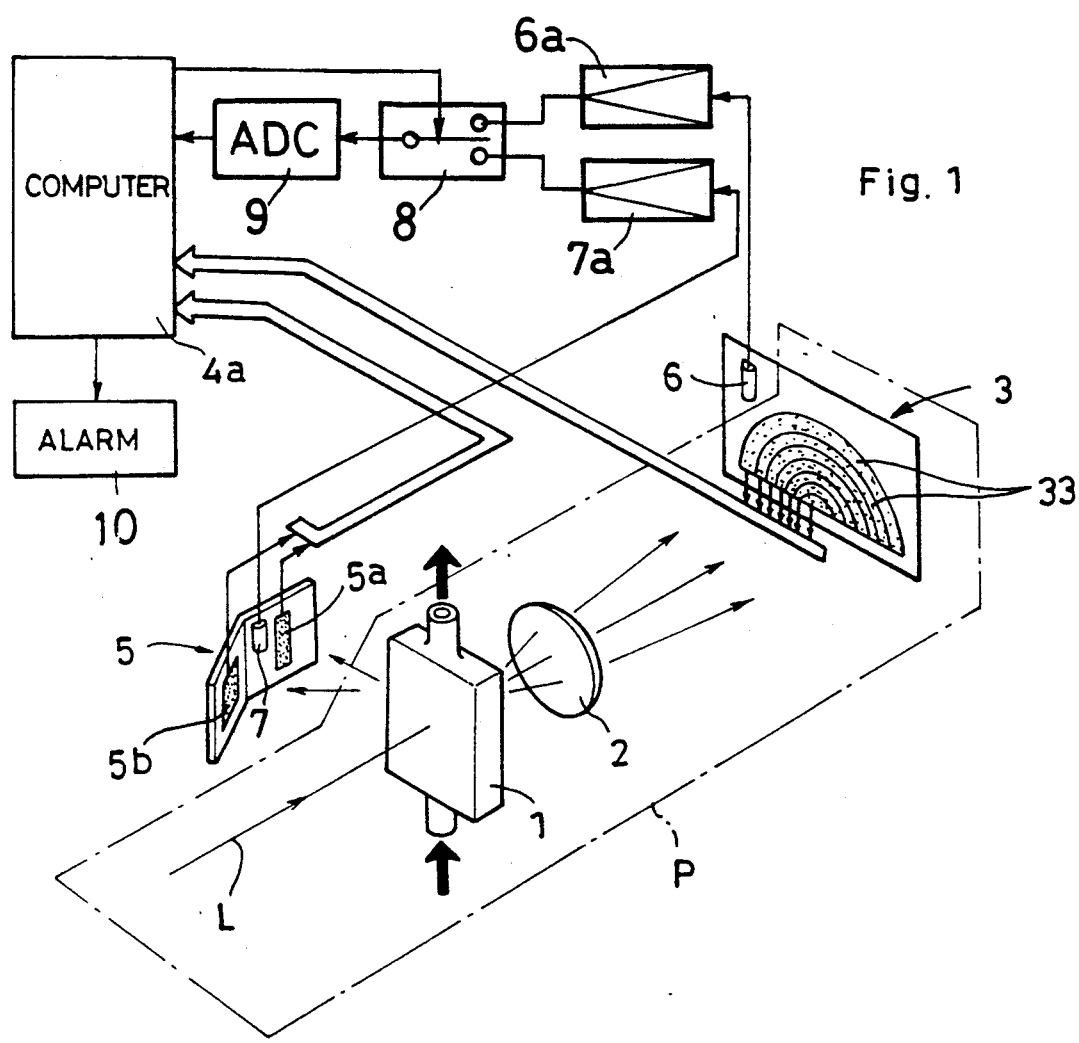
FIG. 1 is a perspective view illustrating the constitution of an embodiment of the present invention.
Figure 5:
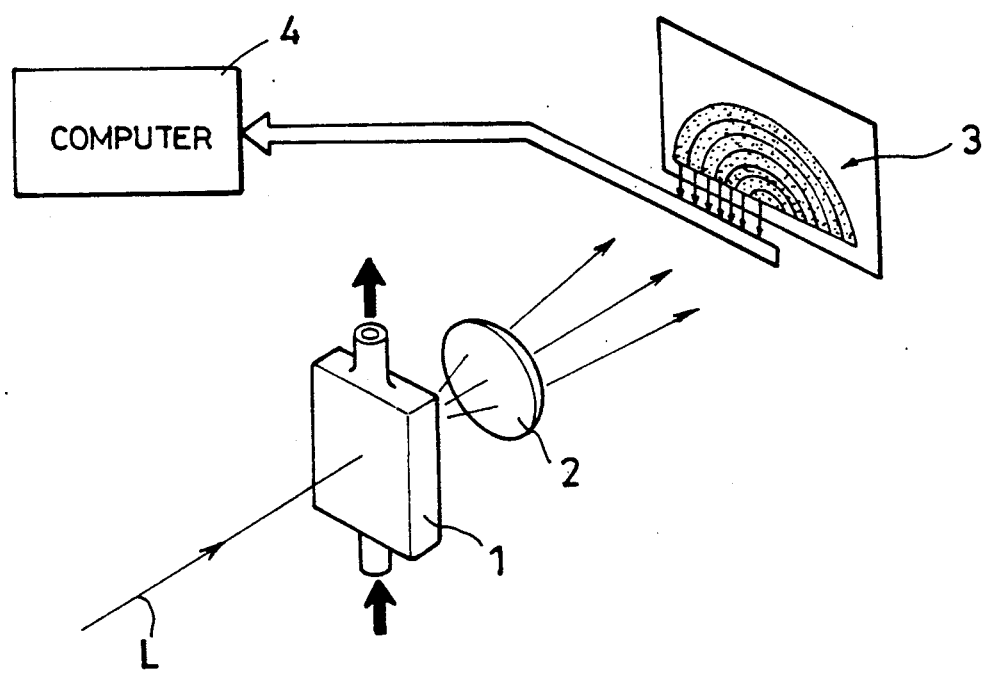
FIG. 5 is a perspective view illustrating the constitution of a conventional optical system for measuring particle size distribution by making use of light scattering.

In FIG. 1, which represents a perspective conceptional constitution of an embodiment of the present invention, a region partitioned by a chain line P corresponds to the previously mentioned conventional apparatus of FIG. 5 with the computer 4 excluded. The embodiment is essentially made up by adding to the conventional apparatus shown in FIG. 5 both a photosensor assembly for detecting lights scattered at large angles and temperature sensing means for detecting temperatures of the resultant two photosensor assemblies in use in this embodiment.

Referring to FIG. 1, a thin light beam L arranged by a not-shown optical system including a laser is applied to a a transparent flow-cell through which sample particles are flowing suspended in a medium fluid. Irradiated by the light beam L the sample particles scatter the light in every direction. Of the scattered rays of light, part of the forward scattered component, a rectangularly scattered component and part of the backward scattered component are detected respectively by a first photosensor assembly 3, by a photosensor 5a and by a photosensor 5b, which, combined with the photosensor 5a, forms a second photosensor assembly 5. The first photosensor assembly 3, which corresponds to the sole photosensor assembly in the conventional apparatus shown in FIG. 5, is made up of a plurality of concentrically arrayed semi-circular photosensors 33. The outputs from all of the photosensors 33, 5a and 5b are, as data signals for particle-size distribution measurement, transfered to a computer 4a, which computes, according to the data signals, the size-distribution of the sample particles. The mathematical method and process of deriving the size distribution are not described in this specification, since they are the same as the conventional in principle, standing outside the objects of the present invention. With the second photosensor assembly 5 (photosensors 5a and 5b) added for detecting sideward and backward scattered lights, the apparatus has its senitivity increased so as to cover very small particles having a size of the order of 0.1 μm.

Figure 3:
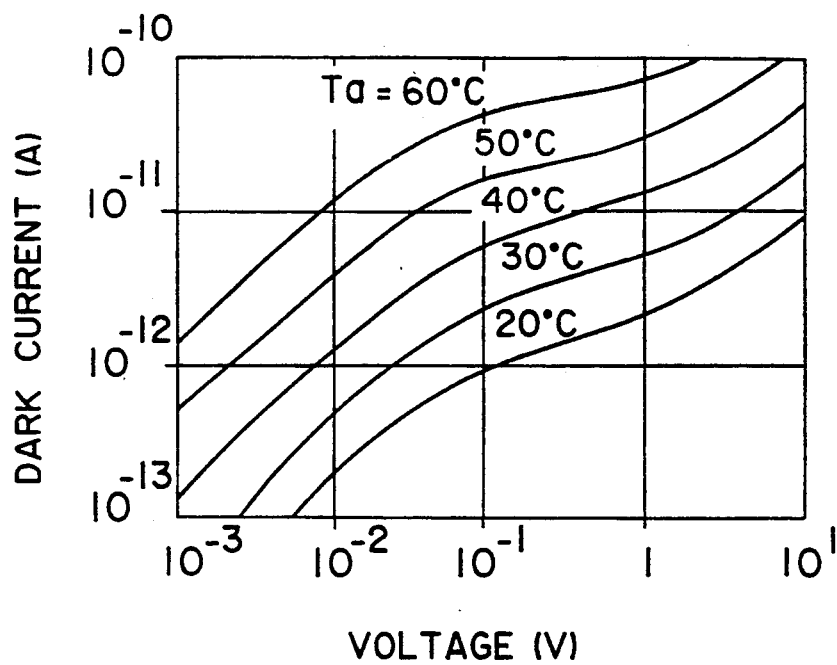
FIG. 3 graphically shows a typical temperature-dependent dark-current characteristic of a photodiode used in the photosensors of the embodiment shown in FIG. 1.
Figure 4:
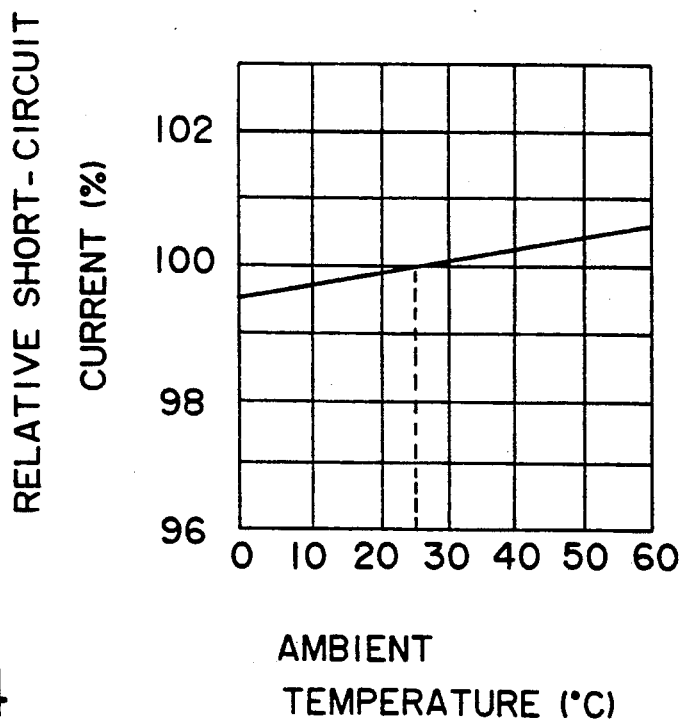
FIG. 4 graphically shows a typical temperature-dependent short-circuit current characteristic of a photodiode used in the embodiment shown in FIG. 1.

However, the lights scattered at such large angles as 90° or larger has their intensities, as is mentioned previously, decreased to 1 lux or lower, causing the output signals of the photosensors 5a and 5b to be of such low level that temperature-influenced small zero-level shift (refer to FIGS. 3 and 4) of any one of the photosensors 5a, 5b and 33 can not be ignored.

Figure 2:
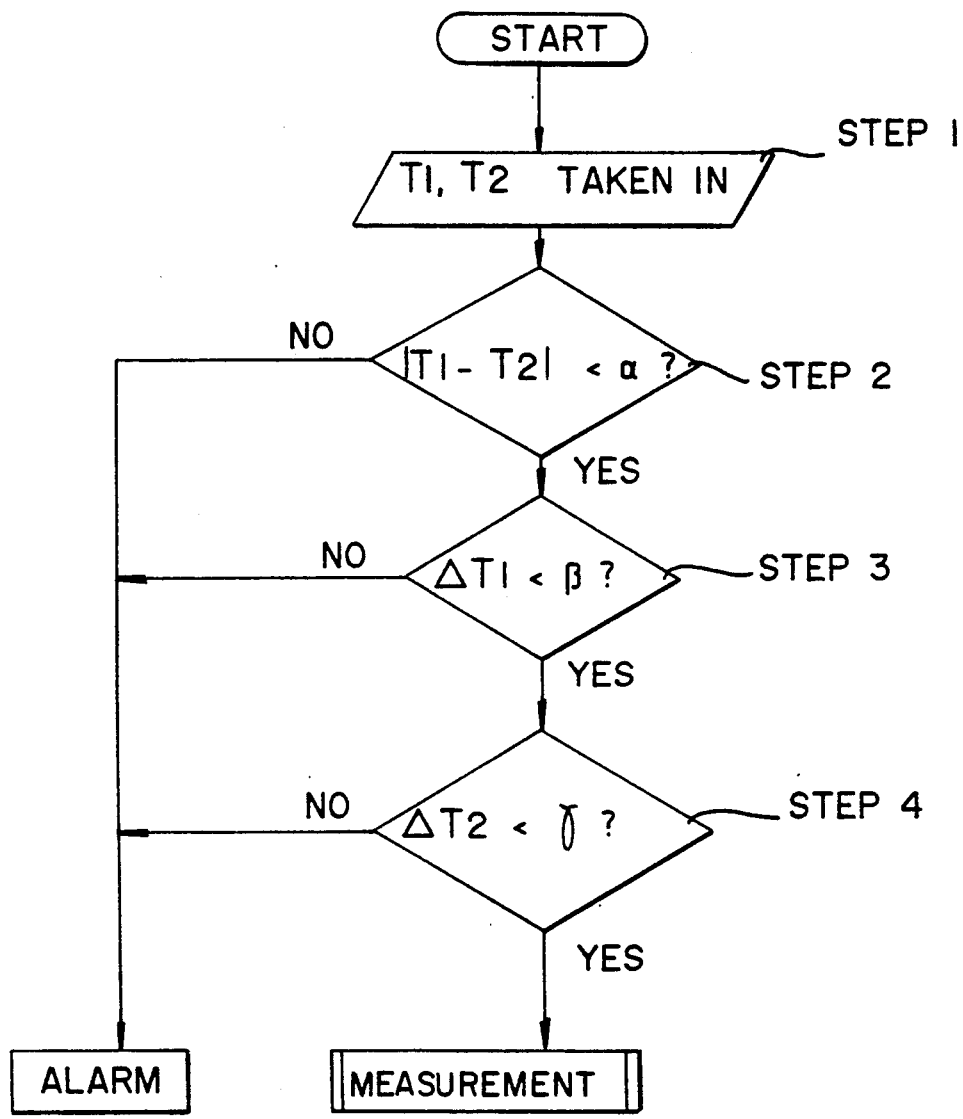
FIG. 2 shows a flow chart of the alarm function added in the present invention.

Therefore, it is inevitable to provide any means for preventing the apparatus from continuing an erroneous measurement operation when the photosensors have their zero-levels varied over a predetermined allowable condition owing to ambient temperature variations which may occur during a process of size distribution measurement. For the purpose the sensor assemblies 3 and 5 are provided with temperature sensors 6 and 7, respectively, for monitoring their respective instantaneous temperatures $T_1$ and $T_2$. The outputs from the temperature sensors 6 and 7, amplified by their respective corresponding amplifiers 6a and 7a, are alternately inputted as temperature data to the computer 4a through a computer-controlled switching means 8 and an analog-to-digital (A-D) converter 9. As is illustrated in FIG. 2, with the temperature data (represented by $T_1$, $T_2$ in the flow chart) taken in (at step 1), the computer 4a judges whether or not an absolute difference $|T_1-T_2|=\Delta T$ and absolute temperature variations $\Delta T_1$ and $\Delta T_2$ remain below their respective predetermined values $\alpha$, $\beta$ and $\gamma$. If any one of $\Delta T$, $\Delta T_1$ and $\Delta T_2$ is judged at step 2, 3 or 4 to reach or exceed the corresponding predetermined value ($\alpha$, $\beta$ or $\gamma$), the computer 4a generates an electric alarm signal toward an alarm display 10. With the signal inputted, the alarm display 10 generates an acoustic and/or visual alarm signal advising an operator to readjust the zero-level of the photosensors. If $\Delta T$, $\Delta T_1$ and $\Delta T_2$ are judged at steps 2, 3 and 4 to remain below their respective predetermined values $\alpha$, $\beta$ and $\gamma$, the process of particle size distribution measurement is continued.

This embodiment can be modified so that the readjustment of zero-level is automatically executed by the computer 4a.

I claim:

1. An apparatus for measuring a particle size distribution through the measurement of intensity distribution of light rays scattered from particles irradiated with a laser beam, said apparatus comprising:

a transparent sample vessel for accepting a fluid medium suspending therein sample particles whose size distribution is to be measured, said transparent sample vessel being irradiated with a laser beam;

a first photosensor assembly consisting of a plurality of concentrically arrayed semicircular photosensors for detecting the intensity distribution of light scattered forward by said sample particles;

a second photosensor assembly consisting of photosensors for detecting lights scattered at angles larger than the scattering angle of said light scattered forward;

a first temperature sensor for sensing the temperature $T_1$ of said first photosensor assembly;

a second temperature sensor for sensing the temperature $T_2$ of said second photosensor assembly;

means for generating an alarm signal when a temperature variation $\Delta T_1$ of said first photosensor assembly, a temperature variation $\Delta T_2$ of said second photosensor assembly or a temperature difference $|T_1-T_2|$ between said first and said second photosensor assemblies reaches or exceeds a predetermined value.

2. An apparatus as difined in claim 1, wherein said second photosensor assembly consists of a photosensor for detecting light scattered at an right angle and of a photosensor for detecting light scattered backward.

* * * * *